United States Patent [19]

Mozdzen

[11] Patent Number: 4,503,273
[45] Date of Patent: Mar. 5, 1985

[54] HYDROGENATION OF PHENOLS

[75] Inventor: Edward C. Mozdzen, Bartlesville, Okla.

[73] Assignee: Phillips Petroleum Company, Bartlesville, Okla.

[21] Appl. No.: 427,219

[22] Filed: Sep. 29, 1982

[51] Int. Cl.$^3$ .............................................. C07C 35/21
[52] U.S. Cl. .................................... 568/816; 568/822; 568/830
[58] Field of Search ............... 568/817, 811, 814, 830, 568/816, 822

[56] References Cited

U.S. PATENT DOCUMENTS

| | | | |
|---|---|---|---|
| 1,593,081 | 7/1926 | Jordan | 568/816 |
| 2,100,468 | 11/1937 | Martin et al. | 568/816 |
| 2,118,954 | 5/1938 | Thomas | 260/153 |
| 2,350,361 | 6/1944 | Major et al. | 568/816 |
| 3,278,611 | 10/1966 | Dewhirst et al. | 568/816 |
| 3,405,185 | 10/1968 | Hulihan et al. | 568/830 |
| 3,759,843 | 9/1973 | Holscher et al. | 252/459 |
| 3,965,187 | 6/1976 | Little et al. | 260/586 R |
| 4,001,343 | 1/1977 | Gaillard | 260/817 |
| 4,053,524 | 10/1977 | Stapp et al. | 260/817 |
| 4,058,571 | 11/1977 | Biedermann | 568/830 |
| 4,088,703 | 5/1978 | Yeh et al. | 568/835 |
| 4,192,960 | 3/1980 | Hillion et al. | 568/816 |
| 4,258,268 | 3/1981 | Bjornson | 568/816 |

FOREIGN PATENT DOCUMENTS

| | | | |
|---|---|---|---|
| 688545 | 6/1964 | Canada | 568/817 |
| 2809995 | 9/1978 | Fed. Rep. of Germany | 568/816 |
| 1074730 | 7/1967 | United Kingdom | 568/816 |

Primary Examiner—Werren B. Lone
Attorney, Agent, or Firm—Howard D. Doescher

[57] ABSTRACT

The hydrogenation of phenolic molecules can be more effectively carried out using pretreated Group VIII catalysts.

13 Claims, No Drawings

HYDROGENATION OF PHENOLS

BACKGROUND

The reaction of phenol or phenolic derivatives, such as bisphenol A, with hydrogen produces useful chemical compounds. Among these phenols are 2,2'-bis (4-hydroxycyclohexyl)propane which, when aminated, yields 2,2'-bis(4-aminocyclohexyl)propane (PACP), an intermediate in the production of engineering plastics.

THE INVENTION

The invention rests on the discovery that certain catalysts can be made more effective for the hydrogenation of phenols and phenolic derivatives by pretreating them with particular solvent/promoter combinations.

In one embodiment the hydrogenation of bisphenol A was carried out using a supported nickel catalyst which had been pretreated with methanolic sodium hydroxide. Compared to the same hydrogenation using an untreated catalyst, significant improvements in selectivity and reaction time were noted.

ADVANTAGES

Using the catalyst and the catalytic hydrogenation process of this invention, several advantages are attained. Most notably, the selectivity of the hydrogenation toward the desired product is increased. Furthermore, the time needed to complete the hydrogenation reaction can be reduced by as much as 50 percent.

OBJECTS OF THE INVENTION

It is one object of the invention to provide a novel hydrogenation catalyst.

It is another object of the invention to provide a novel process for the hydrogenation of phenols and/or phenolic derivatives.

DESCRIPTION OF THE INVENTION

The Catalyst

The catalyst of the invention is produced by contacting a Group VIII metal-containing composition with at least one promoting combination of a non-aqueous organic solvent and a base.

The metal-containing composition of this invention comprises at least one Group VIII metal which is active for the hydrogenation of phenolic molecules supported on or in admixture with a support or solid diluent. The support or solid diluent employed is substantially inert for the hydrogenation of phenolic molecules.

It is believed that the improved selectivity obtained in the practice of the invention is due to the neutralization of acidic sites of the support or solid diluent employed. Thus, the use of supports or solid diluents with acidic character is contemplated. Suitable materials are silica, alumina, silica-alumina, aluminum phosphate, calcium phosphate, zinc aluminate, and zinc titanate. Alumina is preferred as a support or solid diluent.

The support or solid diluent material can be present in the amount of 1 to 99 wt percent, based on the total catalyst weight.

Useful metals encompass all of the metals recited in Group VIII of the Periodic Table. Preferred metals are nickel, palladium, and platinum. Nickel is highly preferred.

Useful promoting combinations are mixtures or solutions of non-aqueous organic solvents with alkaline reagents.

Suitable alkaline materials for use in the promoting mixtures of the invention are materials of essentially basic character. Useful alkaline agents include organic and/or inorganic bases and combinations thereof.

A preferred group of bases are the oxides, hydroxides, carbonates, and other salts or alkali or alkaline earth metals. Particularly useful are the hydroxides of these metals such as, calcium hydroxide, magnesium hydroxide, potassium hydroxide, and sodium hydroxide. Sodium hydroxide is highly preferred.

Mixtures of two or more alkaline reagents, as well as mixtures of alkaline reagents with other conventional ingredients, can be used.

Suitable non-aqueous solvents are those in which the alkaline reagents employed are appreciably soluble. Typically, such organic solvents will include those solvents with polar functional groups. Exemplary classes of solvents are alcohols, esters, polyethers, amides, sulfones, and chlorinated hydrocarbons. Preferred solvents are alcohols.

Suitable alcohols include mono- and poly-hydroxy hydrocarbons. The preferred alcohols contain from 1 to about 20 carbon atoms. Suitable alcohols include methanol, ethanol, n-propanol, and isopropanol. Methanol is highly preferred.

Mixtures of two or more alcohols and mixtures of alcohols with other conventional ingredients can be used.

The proportions in which the alkaline reagent and the Group VIII metal-containing composition are combined may be determined by the skilled artisan. As guidelines, it is suggested that they be employed in molar ratios of 0.01/1 to 1000/1, with 1/1 to 100/1 preferred. Since the addition of alkaline reagent is believed to reduce the incidence of undesirable side reactions promoted by the catalyst support or diluent, more alkaline reagent will be employed for a catalyst with low metal loading, while less alkaline reagent would be required for a catalyst with higher metal loading.

The amount of organic solvent employed to carry out the inventive treatment is not critical. Sufficient organic solvent is employed to ensure complete dissolution of the alkaline reagent employed. Generally, organic solvent to alkaline reagent weight ratios of about 1/1 to 100/1 will be suitable.

The Phenolic Reactant

The phenolic molecules to be hydrogenated in accordance with this invention include a variety of hydroxy-substituted aromatic compounds. Suitable molecules include, phenol, methylphenols, and diphenol alkanes. Bis(4-hydroxyphenyl)alkanes are preferred reactants. 2,2'-Bis(4-hydroxyphenyl)propane is highly preferred.

Mixtures of phenolic reactants can be employed.

The amount of catalyst to be used based on moles of active Group VIII metal will generally lie between about 3.0 and 80 mol %, based on the weight of the phenolic reactant.

Reaction Conditions

Conditions suitable for the hydrogenation of phenolic molecules are well known in the art. It would require only routine experimentation to arrive at suitable parameters to be used when employing the catalyst of this invention.

Typical operating temperatures of about 175°–250° C. are employed, with hydrogen pressures of 1000–2000 psig. Typically reaction times of 1–4 hours are employed in order to achieve quantitative or nearly quantitative conversion of the reactant phenol.

EXAMPLES

All hydrogenation reactions were carried out in either a 300 mL or 1 L stainless steel Autoclave Engineers Inc. stirred tank reactor. The substrate, 2,2'-bis(4-hydroxyphenyl)propane, more commonly called bisphenol A or BPA, catalyst (commercially available Calsicat E-217TR ® which is 50% Ni on $Al_2O_3$, or a base-modified Calsicat ®), and solvent (as specified for each run) were all placed into the autoclave, which was then sealed. Reactor contents were then purged four times by pressuring to 500 psig with $N_2$, then venting, followed by four 500 psig pressure/vent cycles with $H_2$. System pressure was then raised to 1000 psig with $H_2$, and heating and stirring begun. When the desired reaction temperature was reached, $H_2$ pressure was further increased to the desired operating level, which was maintained by intermittent introduction of $H_2$. In the tables which follow, the upper pressure limit defines the target reaction pressure while the lower pressure defines the point at which additional $H_2$ would be introduced.

After the desired reaction time had elapsed, the reactor was allowed to cool to room remperature and then the pressure discharged. The sample was filtered to remove catalyst, which was washed with warm methanol. The methanol wash was added to the filtrate, and the mixture then stripped of solvent on the rotary evaporator. Solid product, 2,2'-bis(4-hydroxycyclohexyl)propane or hydrogenated bisphenol A (abbreviated as HBPA) was obtained upon complete removal of solvent. Solid product was redissolved in methanol for gas liquid chromatography (glc) analysis.

All glc analyses were carried out employing a Pelkin-Elmer Model 900 Gas Chromatograph equipped with a flame ionization detector. Crude samples, prepared as described above, were analyzed on a 4 foot×⅛ inch Tenax GC column at 275° C. Silylated samples (see procedure below) were analyzed on a 2 foot×⅛ inch 10% SE-30 on Chrom P-AW (60/80) mesh). A temperature program was employed for analysis of silylated materials starting at 150° C. which was held for 4 minutes, followed by a 16°/min. program rate to 200° C., which was held for 16 minutes.

EXAMPLE I

For all of the runs tabulated below (Table I), 100 mL solvent, 4 g catalyst (Calsicat E-217TR ® Ni on $Al_2O_3$), and 25 g bis-phenol A were charged into the 300 mL stainless steel autoclave. The general reaction procedure and workup described above was followed.

TABLE I

| Control Runs for the Hydrogenation of Bisphenol A (BPA)* | | | | | |
|---|---|---|---|---|---|
| Solvent | Press., psig | Temp., °C. | Time, hr | BPA Conv., mol % | HBPA Sel.** mol % |
| Diglyme | 1000–1400 | 200 | 1 | 100 | 75.0 |
| Diglyme | 1000–1100 | 200 | 2 | 100 | 88.5 |
| Monoglyme | 1200–1350 | 200 | 1 | 100 | 84.6 |
| 2-Ethoxyethanol | 1000–1350 | 200 | 2 | 100 | 94.6 |
| Isobutanol | 1300–1500 | 200 | 2 | 100 | 92.8 |
| Decalin | 1200–1500 | 225 | 2 | 100 | 94.4 |

TABLE I-continued

| Control Runs for the Hydrogenation of Bisphenol A (BPA)* | | | | | |
|---|---|---|---|---|---|
| Solvent | Press., psig | Temp., °C. | Time, hr | BPA Conv., mol % | HBPA Sel.** mol % |
| Diglyme | 1100–1550 | 200 | 1 | 100 | 66.8 |

*Catalyst was suspended in 200 ml of methanol, filtered and washed with methanol.
**Selectivity These control runs demonstrate that reaction time in excess of one hour is required for greater than 90% yield of hydrogenated bisphenol A.

EXAMPLE II

The procedure employed for example I was repeated, except base-treated Calsicat E-217TR ® Ni on $Al_2NO_3$ was employed as catalyst. The base treatment of catalyst was accomplished by stirring together for one hour a mixture of 10 g NaOH and 10 g Ni catalyst in 200 mL methanol. Catalyst was then filtered and washed several times with dry methanol, and finally air dried before weighing for addition to the reactor. Results are tabulated in Table II.

TABLE II

| Inventive Runs for Hydrogenation of Bisphenol A Employing Base Treated Nickel Hydrogenation Catalyst | | | | | |
|---|---|---|---|---|---|
| Solvent | Press., psig | Temp., °C. | Time, hr | BPA Conv., mol % | HBPA Sel.* mol % |
| Diglyme | 1200–1500 | 200 | 1 | 100 | 93.4 |
| Isobutanol | 1000–1350 | 200 | 1.5 | 100 | 94.4 |
| Decalin | 1300–1500 | 200 | 1 | 99+ | 96.7 |

*Selectivity

These inventive runs demonstrate the high yields of hydrogenated bisphenol A obtained in only 1–1.5 hours by employing the inventive catalyst base treatment in a variety of hydrocarbon and oxygenated organic solvents. The solvents diglyme (diethyleneglycoldimethyl ether) and Tetralin (tetrahydronaphthalene) are especially useful for ease of further conversion of HBPA to PACP since the same solvent can be subjected to the ammonolysis reaction conditions with little, if any, side-reaction. Alcohol solvent, although useful for the inventive hydrogenation reaction, is not a desirable solvent for the further conversion of HBPA to PACP by ammonolysis.

EXAMPLE III

A sequence of hydrogenation reactions were carried out in the 1 L stainless steel autoclave with the same catalyst for all five reactions. The initial run was carried out as described above. 300 mL diglyme, 300 g BPA, and 5 g base-treated catalyst were charged. After the desired reaction time had elapsed, the autoclave and contents were allowed to cool to ~70° C. without stirring. Hydrogen pressure was vented and a nitrogen blanket was introduced. The reactor was opened and 200 mL of reactor liquids were removed, care being taken not to expose any catalyst to air. For subsequent runs, 200 mL fresh diglyme and 25 g. additional BPA were charged. The same catalyst charge (less any catalyst fines lost in product removal) was employed for all runs. The reactor was then resealed and normal $N_2$ and $H_2$ purges, followed by reaction at 200° C., were repeated. Results are tabulated in Table III.

TABLE III

Recycle of Base-Treated Calsicat E-217TR ®

| Press., psig, | Time, Hr. | BPA Conv., mol. % | Sel.** to HBPA, mol % | Sel.** to Partial,* mol % |
|---|---|---|---|---|
| 1200–1550 | 1.5 | 100 | 93.4 | — |
| 1300–1500 | 2.5 | 100 | 92.4 | — |
| 1300–1450 | 2.5 | 100 | 94.3 | 0.1 |
| 1300–1450 | 2.5 | 100 | 89.1 | 6.4 |
| 1350–1550 | 2.5 | 100 | 80.5 | 14.6 |

*Partially hydrogenated BPA.
**Selectivity

These experiments demonstrate that base treated Calsicat E-217TR ® continues to give good hydrogenation yields through several catalyst recycles. The yield of partially hydrogenated BPA becomes significant only after several recycles. This is an indication of reduced catalyst activity rather than reduced selectivity.

EXAMPLE IV

The reaction products from several different hydrogenation reactions were subjected to isomer analysis by a silylation/G.C. procedure. First, 48 mg of product was placed in a vial. To this was added 1 mL pyridine and 1 mL bis-trifluorosilylacetamide. The mixture was gently stirred, then allowed to stand for one hour at room temperature. Samples were then analyzed by G.C. as described above. Product analyses are tabulated in Table IV.

TABLE IV

HBPA Isomer Distribution as a Function of Catalyst Treatment

| | | Reaction | | Isomer Distribution, % | | |
|---|---|---|---|---|---|---|
| Catalyst | Solvent | Time, Hrs. | Temp., °C. | cis, cis | cis, trans | trans, trans |
| Untreated Calsicat ® | Diglyme | 2 | 200 | 10.0 | 40.3 | 49.7 |
| Base-Treated Calsicat ® | Diglyme | 1 | 200 | 10.7 | 43.6 | 45.7 |
| Untreated Calsicat ® | Decalin | 2 | 225 | 7.8 | 44.8 | 47.4 |
| Base-Treated Calsicat ® | Decalin | 1 | 200 | 10.3 | 43.9 | 45.8 |
| Untreated Calsicat ® | Monoglyme | 1 | 200 | 7.5 | 42.8 | 49.7 |
| Untreated Calsicat ® | Isobutanol | 2 | 200 | 8.1 | 41.1 | 50.8 |

The results of these experiments demonstrate that catalyst treatment, reaction time, reaction solvent and reaction temperature have little effect on the isomer distribution of hydrogenated bisphenol A.

Reasonable variations, such as may occur to the routineer in the art, can be made herein without departing from the scope of the invention.

I claim:

1. A process for hydrogenating one or more phenolic molecules comprising contacting same with hydrogen in the presence of a supported catalyst containing a Group VIII metal-containing substance under conditions of temperature, pressure, and reaction time sufficient to achieve quantitative or nearly quantitative conversion of the reactant phenol to hydrogenated phenol, said supported catalyst having been pre-treated with a mixture of an organic solvent having polar functional groups selected from alcohols, esters, polyethers, amides, sulfones and chlorinated hydrocarbons and an alkali or alkaline earth metal alkaline material.

2. The process of claim 1 wherein the phenolic molecule is bisphenol A and the catalyst contains an acidic support or solid diluent and the product is hydrogenated bisphenol.

3. The process of claim 1 wherein the Group VIII metal is selected from the group consisting of nickel, palladium, and platinum.

4. The process of claim 1 wherein the Group VIII metal is nickel.

5. The process of claim 1 wherein said organic solvent is an alcohol having from 1 to about 20 carbon atoms, and said conditions include temperatures of about 175°–250°, hydrogen pressures of 1000–2000 psig, and reaction times of 1–4 hours.

6. The process of claim 5 wherein the alcohol is a $C_{1-6}$ alkanol.

7. The process of claim 6 wherein the alcohol is methanol.

8. The process of claim 7 wherein the support or solid diluent is alumina.

9. A process for hydrogenating phenolic compounds comprising the steps of:
 (1) preparing a catalyst by treating a supported Group VIII-metal containing substance with an organic solvent having polar functional groups selected from alcohols, esters, polyethers, amides, sulfones, and chlorinated hydrocarbons and an alkali or alkaline earth metal alkaline material, and
 (2) contacting at least one phenolic reactant with hydrogen in the presence of the catalyst from step (1) under conditions of temperature, pressure, and reaction time sufficient to achieve quantitative or nearly quantitative conversion of the reactant phenol to hydrogenated phenol.

10. The process of claim 9 wherein said phenolic reactant is bisphenol A and said organic solvent is a $C_{1-6}$ alkanol.

11. The process of claim 10 wherein the alcohol is methanol.

12. The process of claim 11 wherein the Group VIII metal is nickel and the catalyst additionally contains alumina.

13. A process according to claim 9 wherein said hydrogenation is carried out at temperatures of about 175°–250°, hydrogen pressures of 1000–2000 psig, and reaction times of 1–4 hours.

* * * * *